(12) United States Patent
Sano et al.

(10) Patent No.: US 7,374,726 B2
(45) Date of Patent: May 20, 2008

(54) CHEMICAL REACTOR

(75) Inventors: Tadashi Sano, Chiyoda (JP); Ryo Miyake, Tsukuba (JP); Akira Koide, Azuma (JP); Takeshi Harada, Abiko (JP)

(73) Assignee: Hitachi, Ltd., Tokyo (JP)

( * ) Notice: Subject to any disclaimer, the term of this patent is extended or adjusted under 35 U.S.C. 154(b) by 767 days.

(21) Appl. No.: 10/694,810

(22) Filed: Oct. 29, 2003

(65) Prior Publication Data

US 2004/0104162 A1 Jun. 3, 2004

(30) Foreign Application Priority Data

Nov. 1, 2002 (JP) ............................. 2002-319638

(51) Int. Cl.
*B01J 10/00* (2006.01)
*B01L 3/02* (2006.01)

(52) U.S. Cl. ................. 422/129; 422/100; 422/101; 436/178; 210/417; 210/511; 210/321.6; 137/111

(58) Field of Classification Search .......... 422/99–101, 422/129; 436/174, 178; 210/417, 511, 321.6; 137/111

See application file for complete search history.

(56) References Cited

U.S. PATENT DOCUMENTS

| | | | | |
|---|---|---|---|---|
| 5,004,923 | A * | 4/1991 | Hillman et al. .......... 250/341.3 |
| 5,961,832 | A | 10/1999 | Shaw et al. |
| 6,241,379 | B1 | 6/2001 | Larsen |
| 6,884,626 | B1 * | 4/2005 | Borrelli et al. ............ 436/180 |
| 7,091,048 | B2 * | 8/2006 | Parce et al. ............... 436/514 |
| 7,111,652 | B2 * | 9/2006 | Koide et al. .............. 141/104 |
| 7,129,091 | B2 * | 10/2006 | Ismagilov et al. .......... 436/34 |
| 7,214,348 | B2 * | 5/2007 | Desmond et al. .......... 422/101 |

| | | | | |
|---|---|---|---|---|
| 2003/0138819 | A1 * | 7/2003 | Gong et al. ................. 435/6 |
| 2004/0115830 | A1 * | 6/2004 | Touzov ....................... 436/180 |

(Continued)

FOREIGN PATENT DOCUMENTS

JP          64-026125          1/1989

(Continued)

OTHER PUBLICATIONS

Hardt et al., Simulation of Droplet Formation in Micromixers, Journal of Modeling and Simulation of Microsystems, 2001, XP-001160576, pp. 223-226.

(Continued)

*Primary Examiner*—Brian R. Gordon
(74) *Attorney, Agent, or Firm*—Antonelli, Terry, Stout & Kraus, LLP.

(57) ABSTRACT

In a chemical reactor, a gas and a liquid which are in trace volumes are used to produce air bubbles and thus increase the interface area between the gas and liquid, substantially enhancing the efficiency of reaction between the gas and liquid. The chemical reactor comprises the following: a sheath flow forming block which forms a plurality of alternating sheath flows with two mutually unmixable fluids; a plurality of inlet ports through which said two fluids flow into the sheath flow forming block; a contraction zone which simultaneously contracts a plurality of sheath flows formed in the sheath flow forming block; and reaction flow channels each of which is connected with said contraction zone and is smaller in width than the sheath flow forming block.

13 Claims, 8 Drawing Sheets

U.S. PATENT DOCUMENTS

2004/0115838 A1* 6/2004 Quake et al. ............... 436/538
2004/0180377 A1* 9/2004 Manger et al. .............. 435/7.1

FOREIGN PATENT DOCUMENTS

| WO | 96/12541 A1 | 5/1996 |
| WO | 02/089965 A1 | 1/2002 |
| WO | 02/16017 A2 | 2/2002 |
| WO | 03/068381 | 8/2003 |
| WO | 03/099407 A2 | 12/2003 |

OTHER PUBLICATIONS

Tamara M. Floyd et al., Novel Liquid Phase Microreactors for Safe Production of Hazardous Speciality Chemicals, Third International Conference on Microreaction Technology, 2000, pp. 171-180.

* cited by examiner

CHEMICAL REACTOR

FIELD OF THE INVENTION

The present invention relates to a chemical reactor and more particularly to a chemical reactor which allows quick chemical reaction between liquids which cannot be mixed with each other.

BACKGROUND OF THE INVENTION

A device which allows chemical reaction in a microreactor is disclosed by Japanese Patent Laid-Open No. 2000-298079. In this chemical reactor, one flow channel to induce reaction is provided for each liquid. In this method, however, it is difficult to increase the microreactor's throughput on a per-cubic-volume basis. In the reactor, there is only one pair of flow channels and it is easy to separate two liquids which are used for reaction.

Patent Document: Japanese Patent Laid-Open No. 2000-298079

When the sheath flow technique is used for chemical reaction between liquids, a smaller sheath flow width leads to a higher reaction speed. However, when the sheath flow width decreases, the throughput per unit time decreases. Therefore, it is desirable to form multiple sheath flows. After chemical reaction has been made using multiple sheath flows, the two liquids must be separated. However, since they have to be separated outside the microreactor, or in a macro structure, the overall chemical reaction speed will decline.

SUMMARY OF THE INVENTION

The primary object of the present invention is to provide a chemical reactor which enables quick chemical reaction by separating two liquids on a surface where a sheath flow is formed.

In order to achieve the above object, according to a first aspect of the present invention, a chemical reactor comprises the following: a sheath flow forming block which forms a plurality of alternating sheath flows with two mutually unmixable fluids; a plurality of inlet ports through which the two fluids flow into the sheath flow forming block; a contraction zone which simultaneously contracts a plurality of sheath flows formed in the sheath flow forming block; and a reaction flow channel which is connected with the contraction zone and has a width smaller than the width of the sheath flow forming block.

According to a second aspect of the invention, in addition to the first aspect, in the sheath flow forming block, a plurality of inlet ports for one fluid is located in a flow channel for the other fluid.

According to a third aspect of the invention, in addition to the first aspect, a buffer tank with a flow channel sectional area larger than that of the sheath flow forming block is provided upstream of the sheath flow forming block.

According to a fourth aspect of the invention, in addition to the first aspect, a rectifying channel is provided upstream of the contraction zone in each of flow channels for the two fluids.

According to a fifth aspect of the invention, in addition to the first aspect, a plurality of sheath flow forming blocks of the above type are arranged in parallel.

According to a sixth aspect of the invention, in addition to the fifth aspect, the lengths of the flow channels from the plural sheath flow forming blocks to an area of convergence at the downstream are equal.

According to a seventh aspect of the invention, in addition to the first aspect, the reaction flow channel located downstream of the sheath flow forming block has a profile formed with a straight line and a smooth curve.

According to an eighth aspect of the invention, in addition to the first aspect, downstream of the reaction flow channel in which two kinds of fluids having an interface flow, a thin flow channel with a sectional area smaller than that of the reaction flow channel is provided, a thick flow channel with a sectional area larger than that of the reaction flow channel is provided downstream of the thin flow channel, and two outlet ports which differ vertically in height are provided downstream of the thick flow channel.

According to a ninth aspect of the invention, in addition to the eighth aspect, an area adjacent to at least one of the outlet ports is surface-treated.

According to a tenth aspect of the invention, in addition to the first aspect, downstream of the reaction flow channel in which two kinds of liquids having an interface flow, one outlet port is provided for each liquid and a separation film having a plurality of holes with a sectional area of $0.01\ mm^2$ or less is provided between one outlet port and the reaction flow channel.

According to an eleventh aspect of the invention, in addition to the first aspect, downstream of the reaction flow channel in which two kinds of liquids having an interface flow, one outlet port is provided for each liquid, a separation film having a plurality of holes with a sectional area of $1\ mm^2$ or less is provided between one outlet port and the reaction flow channel, and the inside of the holes and an area adjacent to the holes on a flow channel surface in which the holes are made are surface-treated.

According to a twelfth aspect of the invention, in addition to the first aspect, downstream of the reaction flow channel in which two kinds of liquids having an interface flow, one outlet port is provided for each liquid and one hole with a sectional area of $10\ mm^2$ or less is provided between one outlet port and the reaction flow channel.

According to a thirteenth aspect of the invention, in addition to the first aspect, downstream of the reaction flow channel in which two kinds of liquids having an interface flow, one outlet port is provided for each liquid, one hole with a sectional area of $100\ mm^2$ or less is provided between one outlet port and the reaction flow channel, and the inside of the holes and an area adjacent to the hole on a flow channel surface in which the holes are made are surface-treated.

According to a fourteenth aspect of the invention, in addition to the first aspect, the above components are manufactured by microfabrication technology.

DETAILED DESCRIPTION OF THE PREFERRED EMBODIMENTS

Next, chemical reactors according to preferred embodiments of the present invention will be described referring to the accompanying drawings (FIGS. 1 to 7).

Figure 1:
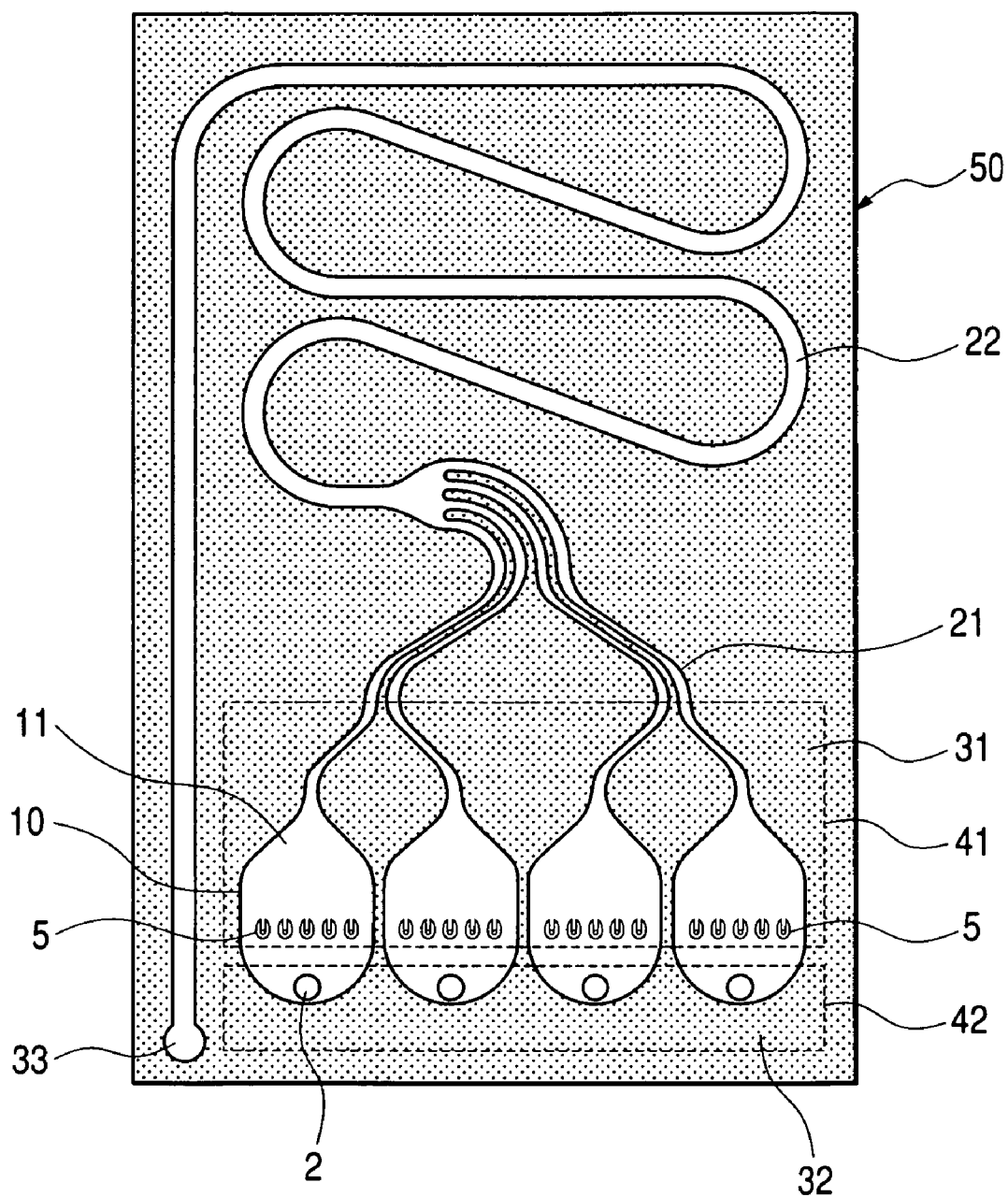
FIG. 1 shows the structure of a chemical reactor according to an embodiment of the present invention.
Figure 2:
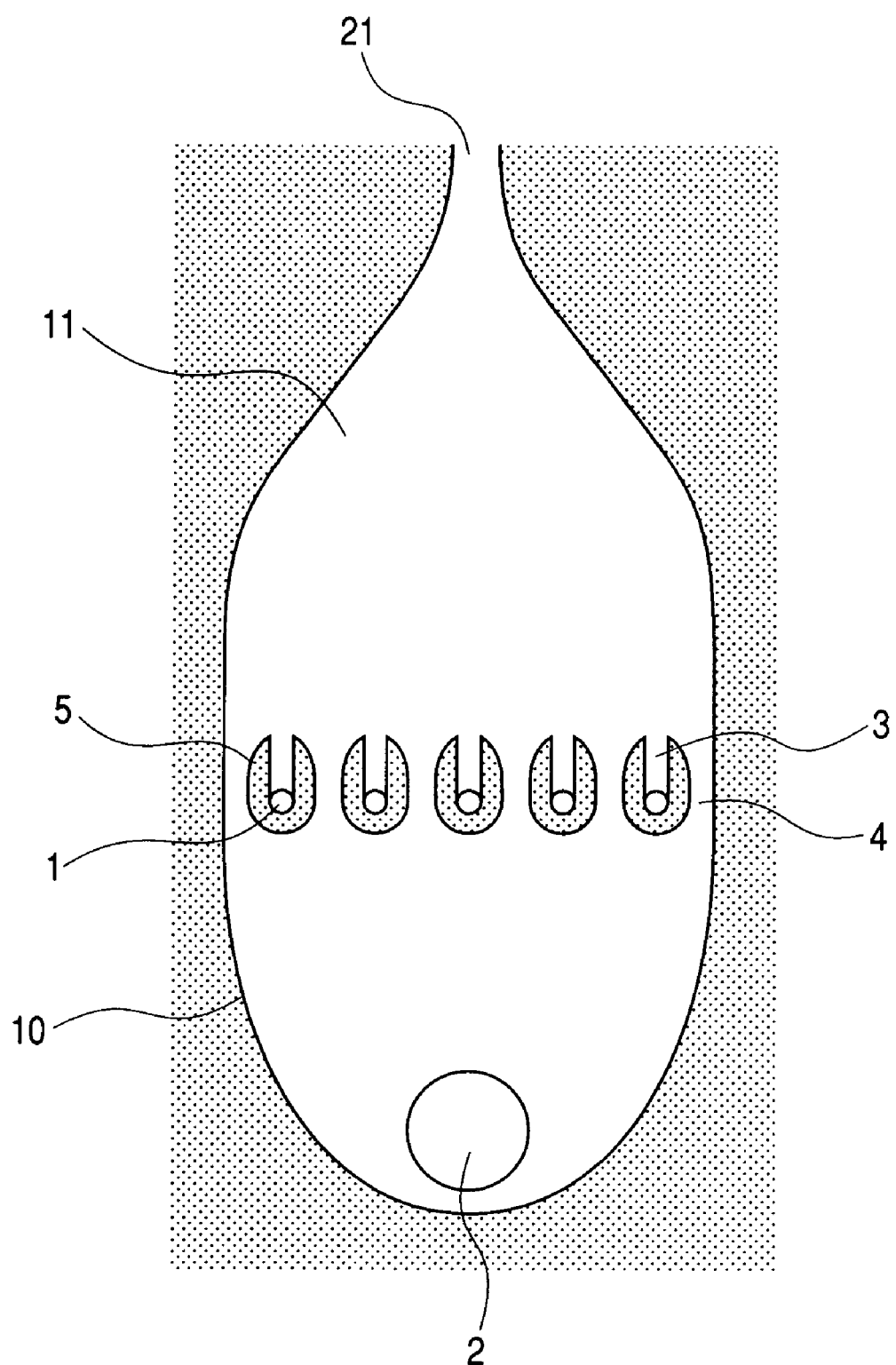
FIG. 2 is a detail view showing a sheath flow forming block in a chemical reactor according to an embodiment of the present invention.
Figure 7:
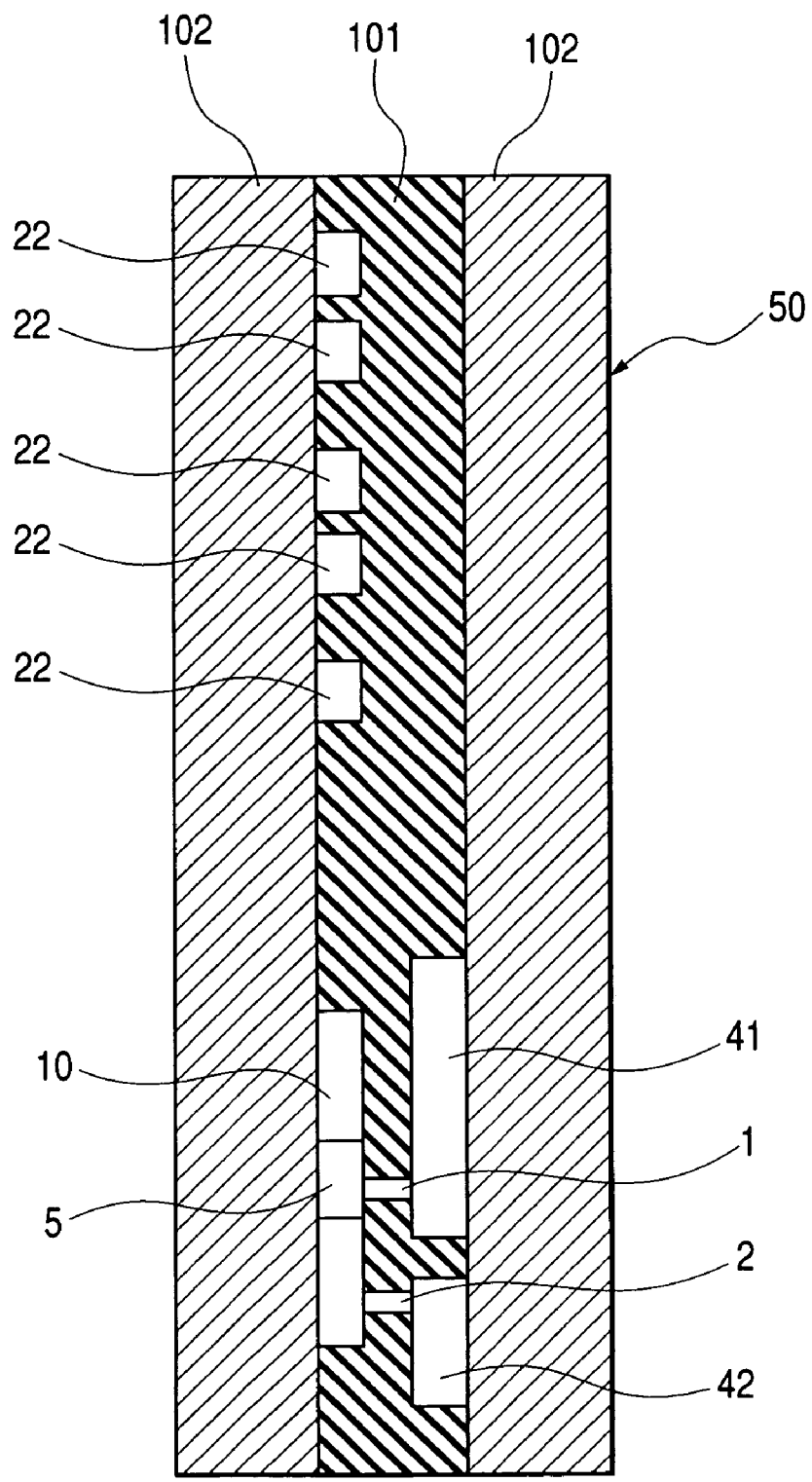
FIG. 7 is a sectional view showing a chemical reactor according to an embodiment of the present invention.

A chemical reactor 50 as shown in FIG. 1 has a structure in which a silicon base 101 with flow channels carved therein is sandwiched between glass covers 102 as shown in FIG. 7. In this chemical reactor 50, two liquids are made into a multiple sheath flow configuration inside a microreactor to induce chemical reaction. After the chemical reaction is over, the liquids which do not mix with each other are separated at high speed inside the microreactor. A glass base and a silicon cover may be used instead of the silicon base 101 and the glass cover 102, respectively. However, the silicon base 101 may be particularly effective as will be explained later.

For solvent extraction by chemical reaction in the chemical reactor 50, an original solvent is led through a connection port 31 (provided on the back side) into a buffer tank 41 as shown in FIG. 1. There are a plurality of buffer tanks 41 (four tanks in the case of FIG. 1) which are adjacent to each other and in a row. The inflowing original solvent passes through an inlet port 1 inside a nozzle 5 and flows into the front side (where a sheath flow forming block 10 lies) to join an extracting solvent through a rectifying channel 3. There are a plurality of nozzles 5 (five nozzles in the case of FIG. 1 and FIG. 2) which are spaced at regular intervals. The nozzles 5 are in a row and connected with each other at the lower part of the buffer tank 41. One inlet port 1 is provided in each nozzle 5. The rectifying channel 3 extends inside the nozzle 5, with its bottom adjoining the inlet port 1 and its top open to the sheath flow forming block 10.

On the other hand, the extracting solvent passes through a connection port 32 (provided on the back side) and flows into a buffer tank 42. The inflowing extracting solvent passes through an inlet port 2 and flows into the front side (where a sheath flow forming block 10 lies) to join the original solvent through a rectifying channel 4. One inlet port 2 is provided in each sheath flow forming block 10 and inlet ports 2, each located at the top of a buffer tank 42, are in a row and connected with each other. The rectifying channels 4, which are formed at regular intervals by gaps between neighboring nozzles 5 and between nozzles 5 and the wall surfaces of the sheath flow forming block 10, extend vertically parallel to the rectifying channels 3.

Figure 3:
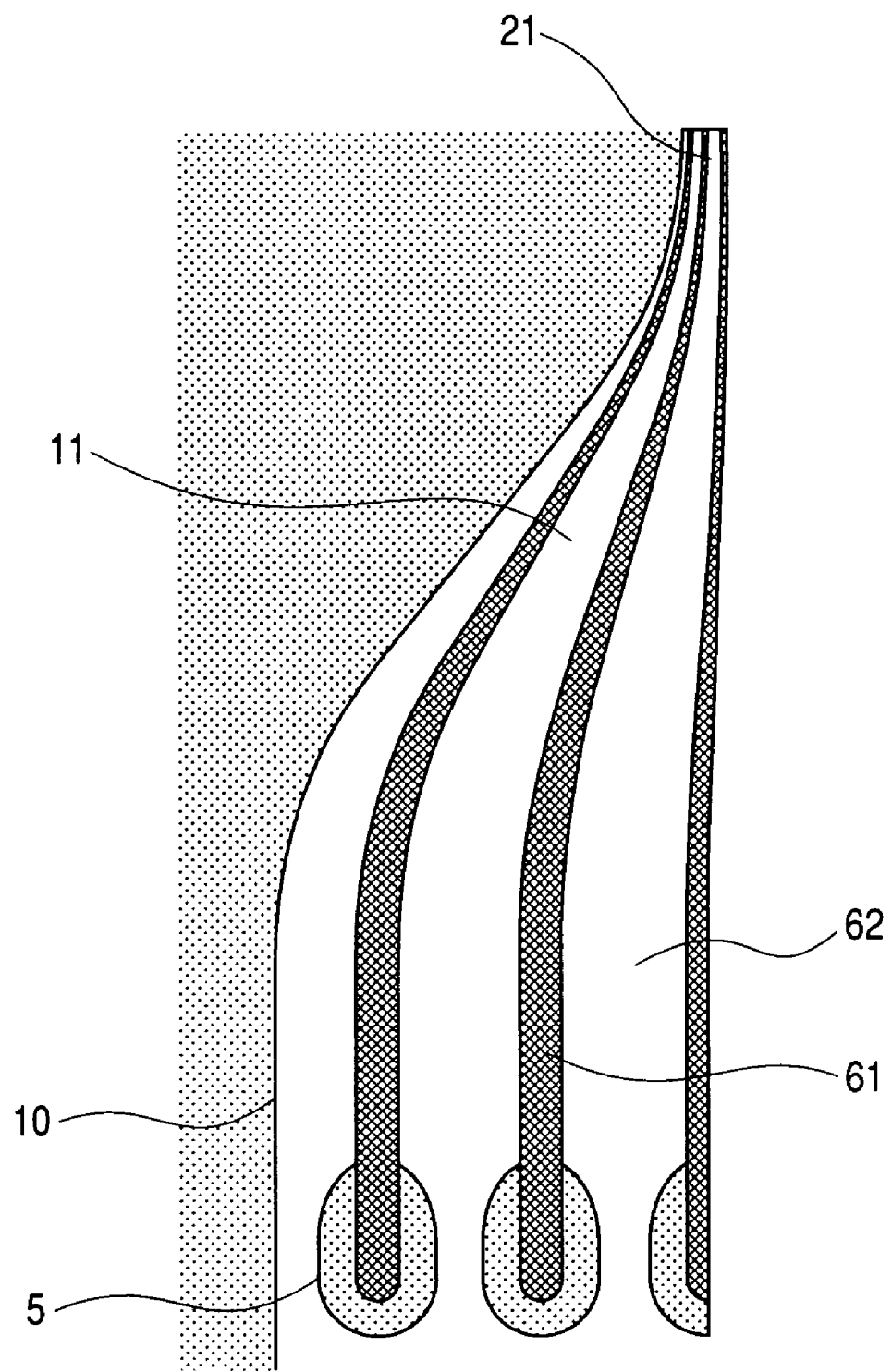
FIG. 3 is another detail view showing a sheath flow forming block in a chemical reactor according to an embodiment of the present invention.

Thus, the buffer tanks 41, buffer tanks 42, rectifying channels 3, and rectifying channels 4 equalize the widths of sheath flows of liquids formed in the sheath flow forming block 10. Since the combined liquids tend to have smaller Reynolds numbers, generally they become laminar flows, forming sheath flows as shown in FIG. 3. The widths of the formed sheath flows are decreased uniformly by contraction channels 11. The speed at which the extract in the original solvent is extracted (extraction speed) drastically increases as the distance between liquids decreases, so extraction reaction begins virtually at the downstream of the contraction channels 11.

While extraction reaction is in progress in the sheath flows, they pass through reaction flow channels 21 arranged in parallel in a way to make the flow channel lengths equal. Since the lengths of the reaction flow channels 21 are equal, the results of extraction are stable with less reaction rate variation.

As each sheath flow advances, it joins a sheath flow formed in another sheath flow forming block 10; while it is going through a reaction flow channel 22, extraction reaction progresses. Since the sheath flow is destroyed at an external connection port 33, the extraction speed suddenly drops and extraction reaction virtually halts.

Next, formation of multiple sheath flows with a small flow width, is described in detail referring to FIG. 3. FIG. 3 shows a condition that an original solvent 61 and an extracting solvent 62 are flowing. The flow width ratio of the original solvent 61 to the extracting solvent 62 after the outlet of the nozzle 5 is determined by the ratio of the inflow rate at the connection port 31 to that at the connection port 32. Therefore, when the inflow rate ratio for the original solvent is increased, the flow width after the outlet of the nozzle 5 is larger than the width of the rectifying channel 3; on the other hand, when the inflow rate ratio is decreased, the flow width after the outlet of the nozzle 5 is smaller than the width of the rectifying channel 3. For both the original solvent and the extracting solvent, the flow width thus adjusted is reduced by the contraction channel 11. The flow width at the downstream of the contraction channel 11 is determined by the ratio of the flow channel width of the sheath flow forming block 10 to that of the reaction flow channel 21. After the flow contraction, the flow width ratio of the original solvent 61 to the extracting solvent 62 remains virtually unchanged, so the sheath flow width of each liquid for extraction reaction is determined by the flow width of each liquid before the flow contraction.

In the chemical reactor 50 according to the present invention, a rectifying channel 3 and a rectifying channel 4 are provided, and a buffer tank 41 and a buffer tank 42 are located upstream of these channels respectively. This permits the original solvent 61 and the extracting solvent 62 to inflow uniformly from the inlet ports 1 and 2 without being exposed to the upstream pressure distribution, contributing to a stable sheath flow formation.

In the sheath flow forming block 10 according to the present invention, several nozzles 5 are located in a flow channel to form multiple sheath flows. This makes it possible to decrease the number of flow channels with small sectional areas or decrease their length, which minimizes loss in the pressure to let liquids flow and makes it easy to manufacture the chemical reactor 50 according to the present invention.

As illustrated in FIG. 1, four sheath flow forming blocks 10 are arranged in parallel. Since a sheath flow is stable in the reaction flow channel 22, more sheath flow forming blocks may be provided. According to the present invention, the number of sheath flow forming blocks is not limited to 4; any number of sheath flow forming blocks may be provided. The optimum number of nozzles 5 in the sheath flow forming block 10 is determined by the viscosities of inflowing liquids, the design width of the reaction flow channel 21, and the intended flow width of the original solvent. When the width of the reaction flow channel 21 is decreased, the intended flow width may be decreased but pressure loss increases. When there are more nozzles 5, the width of the reaction flow channels 21 may be relatively decreased, but it may become necessary to adjust the position of the nozzles 5 because of an increase in the difference between the inner and outer flow channel lengths in the sheath flow forming block 10. Besides, as the number of nozzles 5 is larger, the Reynolds number is larger, which makes it difficult to form a sheath flow stably.

The reaction flow channels 21 and 22 constitute a smooth curve channel with no elbows. Even if there should be elbows, the sheath flow would be maintained because of a small Reynolds number. However, in the case of a smooth curve channel, generation of separation regions is suppressed and errors at the start and end of extraction are minimized.

According to the present invention, a sheath flow can be separated into an original solvent and an extracting solvent in a separation zone 12 and then the liquids are forced out.

Figure 4A:
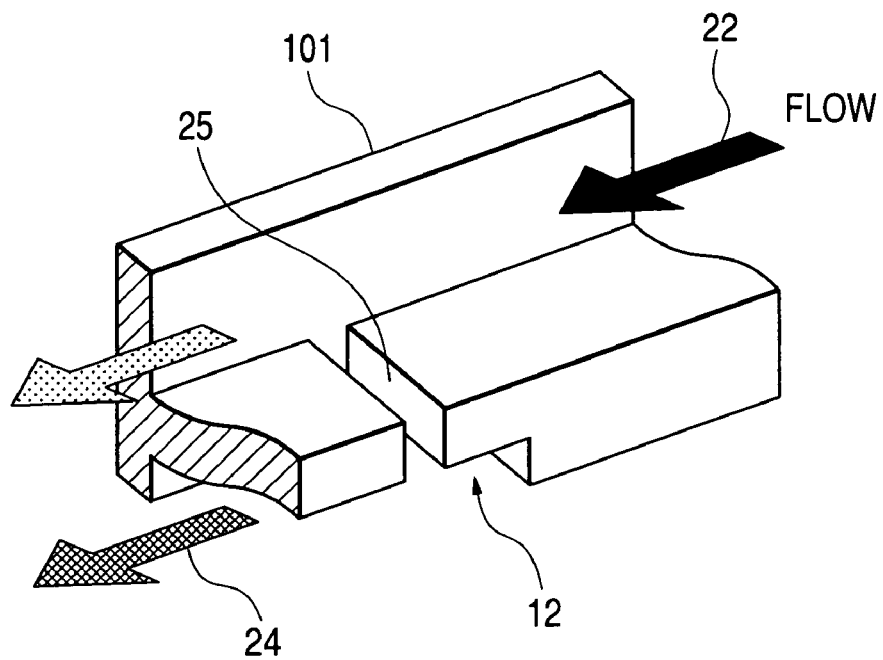
FIG. 4A shows a liquid separation zone in a chemical reactor according to another embodiment of the present invention.
Figure 4B:
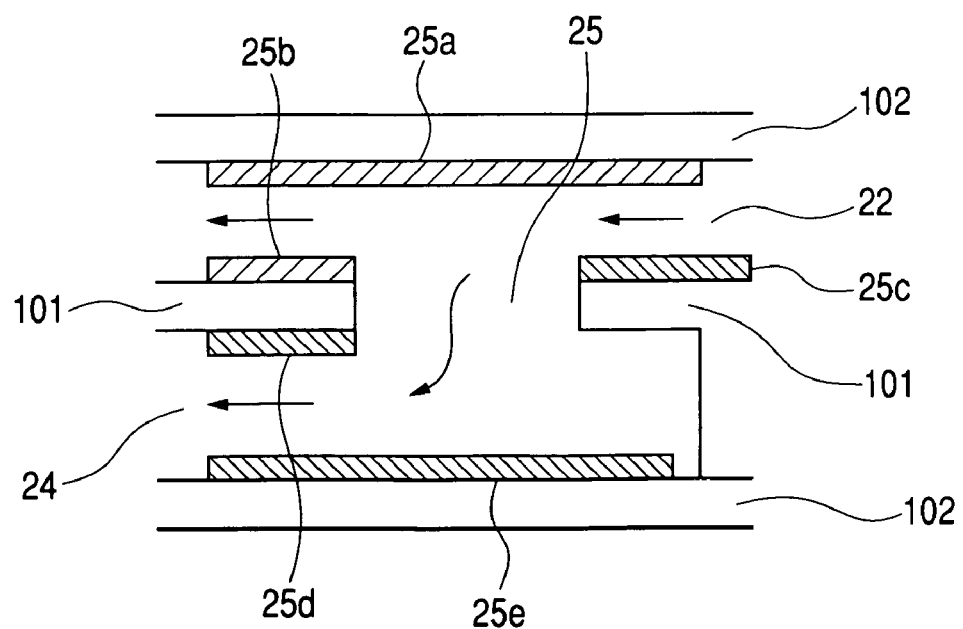
FIG. 4B is a top view showing the separation zone shown in FIG. 4A.

Next, referring to FIG. 4A and FIG. 4B, an example of the separation zone 12 is explained.

The separation zone 12 (FIG. 4A) lies in a through hole 25 midway in the reaction flow channel 22. This through hole 25 is as narrow as 1 mm or less in the moving direction of the reaction flow channel 22. This narrow through hole 25 is connected with the reaction flow channel 22 on the front side of the silicon base 101 and an outlet flow channel 24 on the back side of the silicon base 101. This outlet flow channel 24 is connected with an external flow channel.

The bottom face of the reaction flow channel 22 and the through hole 25 are integral parts of the silicon base 101 and there are hydrophilic oxide layers on their surfaces. Because of this structure, a polar substance such as an aqueous solution coming through the reaction flow channel 22 easily passes through the through hole 25 while a nonpolar substance such as an organic solvent hardly passes through the through hole 25. Hence, when the pressure on the side of the reaction flow channel 22 in the through hole 25 is higher than the pressure on the side of the outlet flow channel 24, the polar substance passes through the through hole 25 and flows into the outlet flow channel 24 and the nonpolar substance such as an organic solvent cannot flow through the through hole 25 and continues flowing in the reaction flow channel 22, thus separating the organic solvent and the aqueous solution. The chemical reactor 50 according to the present invention may be reoriented with respect to the direction of gravity so that the aqueous solution and organic solvent can be easily separated according to the difference between their specific gravities.

When the through hole 25 and the upstream surface of the reaction flow channel 22 in which the through hole is made are hydrophilic-finished (for example, by making a hydrophilic layer on them), the efficiency of the above separation is improved and the flow channel sectional area of the through hole 25 is substantially increased.

Contrary to the above, when the through hole 25 and the upstream surface of the reaction flow channel 22 in which the through hole is made are lipophilic-finished or water-repellent finished (for example, by making a lipophilic layer on them), the organic solvent flows into the through hole 25. Contrary to the above, the aqueous solution cannot flow into the through hole 25. As a result, the organic solvent flows into the outlet flow channel 24 and the aqueous solution continues flowing in the reaction flow channel 22; and the liquids are thus separated. Concretely, as illustrated in FIG. 4B, the surfaces 25a, 25b around the hole at one outlet side are lipophilic-finished or water-repellent finished and the surfaces 25d, 25e around the hole at the other outlet side are hydrophilic-finished so that the organic solvent flows into the outlet flow channel 24 and the aqueous solution continues flowing in the reaction flow channel 22, ensuring that the liquids are separated. In addition, the surface 25c (of the silicon base 101) around the through hole 25 at the inlet side is hydrophilic-finished to increase the efficiency of the above separation. The lipophilic or water-repellent surfaces 25a, 25b and the hydrophilic surfaces 25c to 25e may be used independently or a combination of these may be used.

Figure 5:
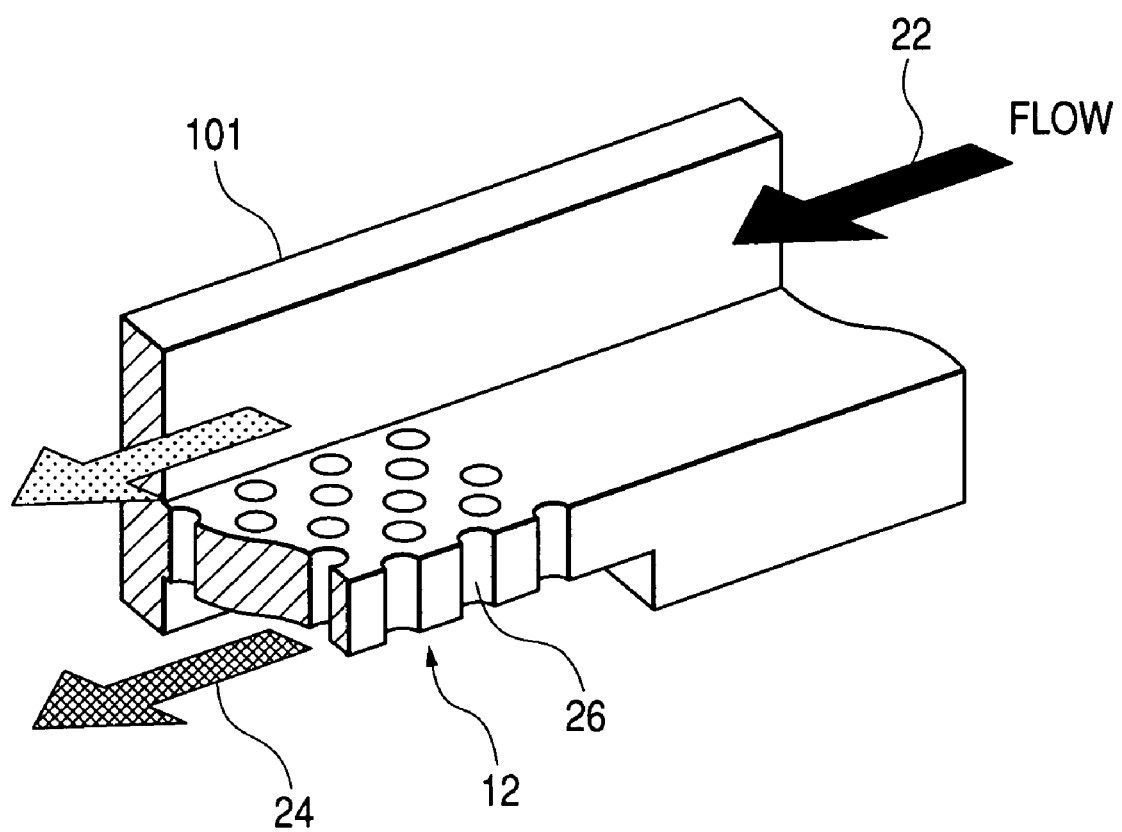
FIG. 5 shows still another example of a liquid separation zone in a chemical reactor according to an embodiment of the present invention.

Next, another example of the separation zone 12 is explained referring to FIG. 5.

The separation zone 12 shown in FIG. 5 consists of plural through holes 26 made midway in the reaction flow channel 22. Each of these through holes 26 is a narrow channel with a sectional area of 0.01 mm$^2$ or less. The through holes 26 connect the reaction flow channel 22 and outlet flow channel 24 which are formed by the silicon base surfaces. The outlet flow channel is connected with an external flow channel. The bottom face of the reaction flow channel 22 and the through holes 26 are integral parts of the silicon base 101, which means that there is a hydrophilic oxide layer on their surfaces.

Because of this structure, a polar substance such as an aqueous solution coming through the reaction flow channel 22 easily passes through the through holes. Hence, when the pressure on the side of the reaction flow channel 22 in the through holes 26 is higher than the pressure on the side of the outlet flow channel 24, the polar substance passes through the through holes 26 and flows into the outlet flow channel 24 and the nonpolar substance such as an organic solvent cannot flow through the through holes 26 and continues flowing in the reaction flow channel 22, thus separating the organic solvent and the aqueous solution. The chemical reactor 50 according to the present invention may be reoriented with respect to the direction of gravity so that the aqueous solution and organic solvent can be easily separated according to the difference between their specific gravities.

When the through holes 26 and the upstream surface of the reaction flow channel 22 in which the through holes 26 are made are hydrophilic-finished (for example, by making a hydrophilic layer on them), the efficiency of the above separation is improved and the sectional area of the through holes 26 is substantially increased.

Contrary to the above, when the through holes 26 and the upstream surface of the reaction flow channel 22 in which the through holes 26 are made are lipophilic-finished or water-repellent finished (for example, by making a lipophilic layer on them), the organic solvent flows into the through holes 26. Contrary to the above, the aqueous solution cannot flow into the through holes 26. As a result, the organic solvent flows into the outlet flow channel 24 and the aqueous solution continues flowing in the reaction flow channel 22; and the liquids are thus separated.

Figure 6:
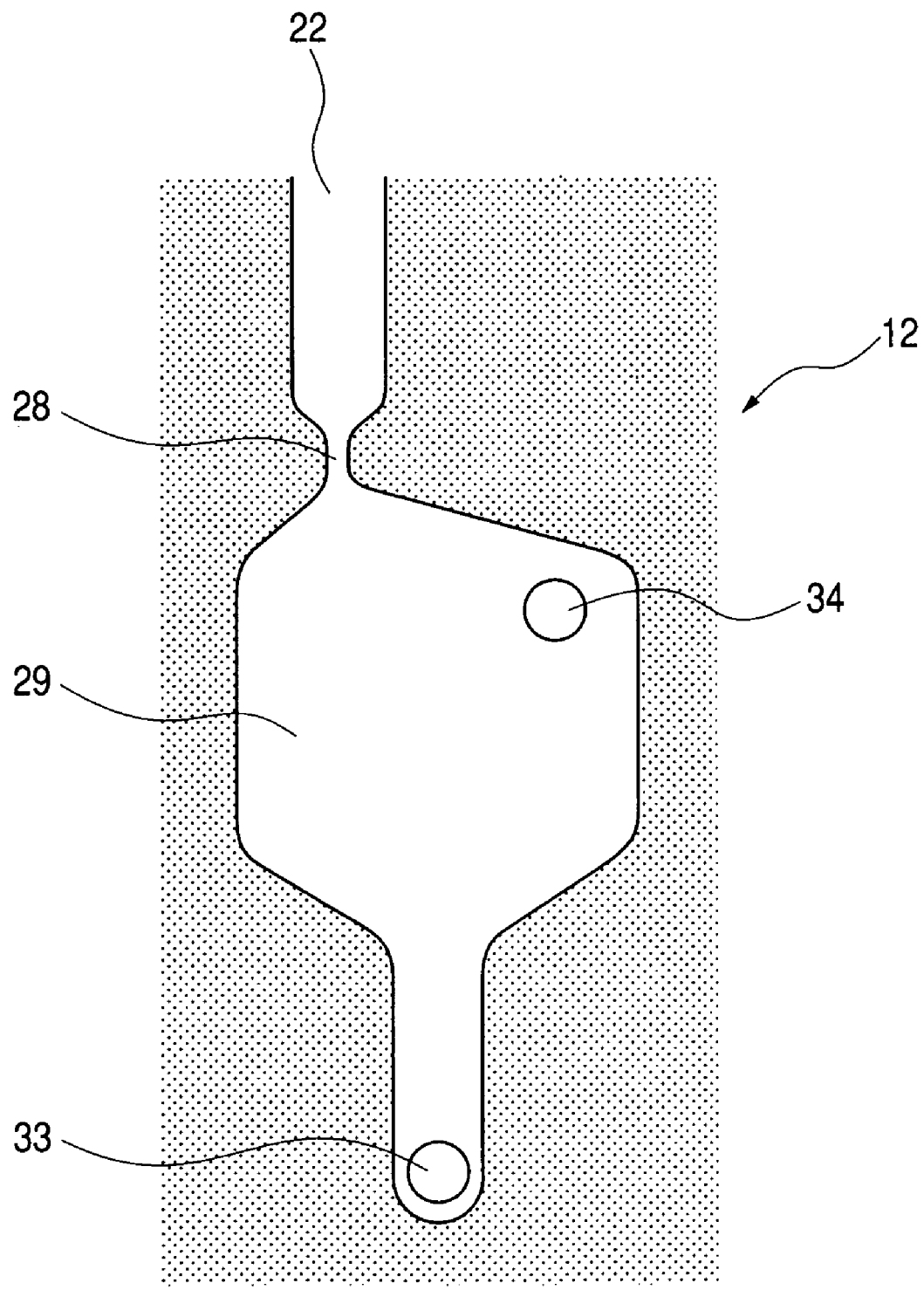
FIG. 6 shows still another example of a liquid separation zone in a chemical reactor according to an embodiment of the present invention.

Next, a further example of the separation zone 12 is explained referring to FIG. 6.

The separation zone 12 shown in FIG. 6 consists of a thin flow channel 28 provided downstream of the reaction flow channel 22. This thin flow channel 28 is a narrow flow channel which has a sectional area of not more than one half that of the reaction flow channel 22 and a channel length almost equal to its width. Downstream of the thin flow channel 28 is provided a settler 29 whose sectional area in the flow channel direction is more than ten times as large as that of the reaction flow channel 22. A connection port 34 is located vertically above a connection port 33 and off an extension of the thin flow channel 28.

In the thin flow channel 28, for the liquids coming through the reaction flow channel 22, their sheath flow form is destroyed and turned into droplets. When the liquids flow into the settler 29 at the downstream, their flow velocity suddenly drops due to the sudden increase in the flow channel sectional area and droplets thus generated touch each other, resulting in droplet size growth. As droplets become larger, the speed of precipitation or settling due to specific gravity differences rapidly rises. This means that the larger the droplets are, the higher the separation efficiency is. In the settler 29, droplets with larger specific gravities gather at the lower side and droplets with smaller specific gravities gather at the upper side. While this condition is maintained, the liquids are continuously pulled out through the connection port 33 and connection port 34 to separate the two different kinds of liquids. The surfaces of the settler 29 may be lipophilic or water-repellent finished, or hydrophilic-finished depending on the liquids flowing out through the connection ports 33 and 34 so that the separation efficiency is further improved.

Any of the abovementioned separation zones 12 according to the present invention may also be used to separate a gas and a liquid. In the separation methods which use a through hole, a gas may pass through the through hole instead of a liquid. In the separation methods which take advantage of specific gravity differences, a gas may be led upwards to go out. In order to further improve the efficiency in separating a gas from a liquid, if the liquid is an organic solvent, the flow channel surfaces for the gas should be hydrophilic, or if the liquid is an aqueous solution, the surfaces should be lipophilic or water repellent.

Figure 8:
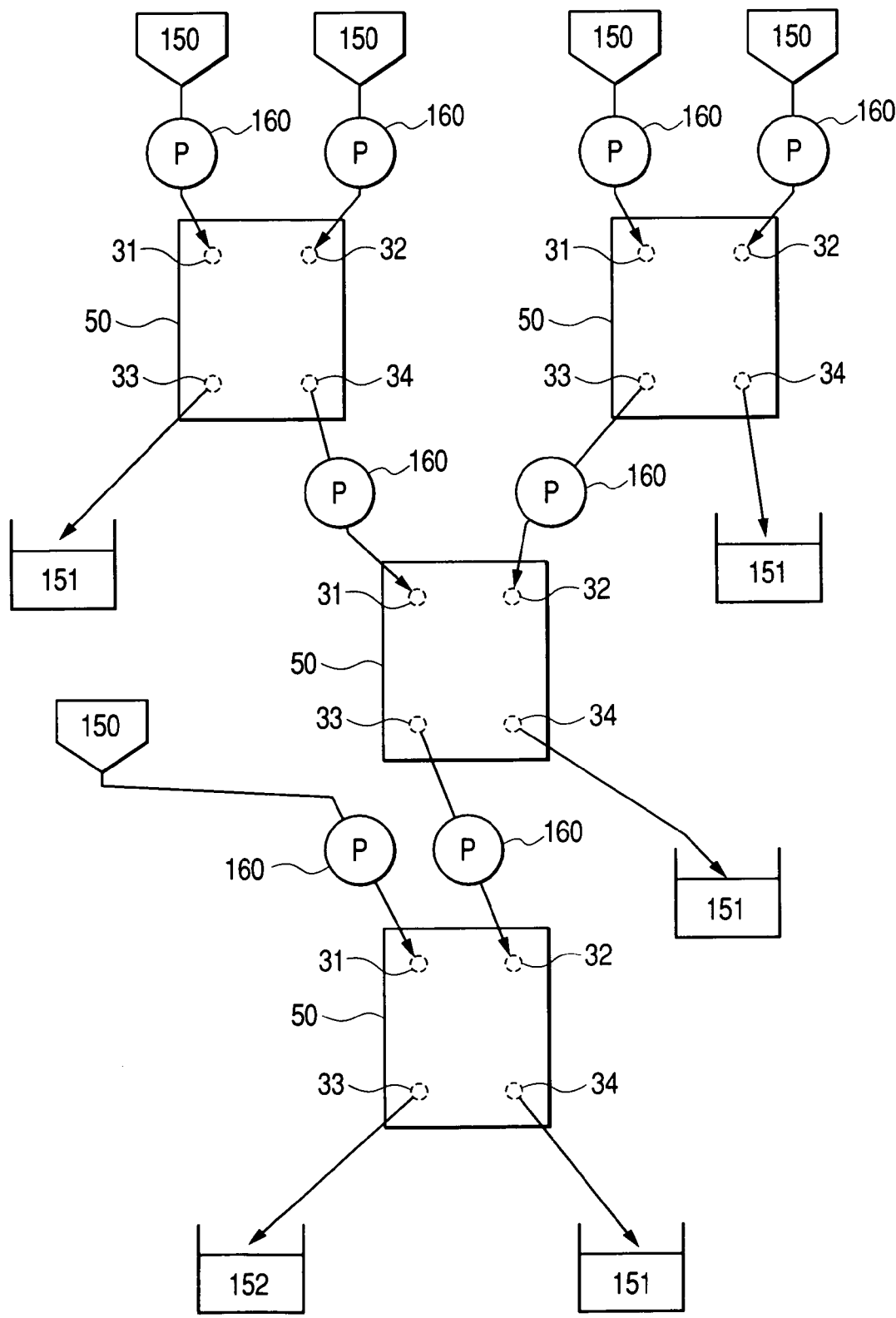
FIG. 8 shows the configuration of a chemical reaction plant according to an embodiment of the present invention.

Next, a chemical processing plant which uses the above chemical reactor 50 is explained referring to FIG. 8. A material stored in a material tank 150 is pressurized by a pump 160 and introduced through connection ports 31 and 32 into a chemical reactor 50. After chemical reaction, the liquid is separated into a waste liquid and a product and the waste liquid is led through the connection port 33 or 34 into a waste liquid tank 151. The liquid as the product is combined with another product or a new material and sent to a next chemical reactor 50 where chemical reaction takes place again. This process is repeated until an intended liquid is collected in a product tank 152.

The pump 160 used here is not indispensable but should be installed as necessary. If temperature control is needed for chemical reaction, the chemical reactor 50 may be surrounded by temperature controllers. In this case, the chemical reactors 50 used here need not be equal; they may be different in flow channel dimensions and shapes depending on the application purpose. Furthermore, a chemical reactor 50 may be combined not with another chemical reactor 50 but with an evaporator, stationary tank or heating tank.

As described above, according to the present invention, a microscopic sheath flow can be formed and after chemical reaction, liquids can be separated, so the time required for reaction of liquids is shortened and thus the required reaction container volume can be reduced. In addition, since reaction can be started without large volumes of flowing liquids, the minimum volumes of liquids required for reaction can be decreased.

As a consequence, peripheral devices for the chemical reactor such as feeding devices may be compact and there is flexibility in determining where to install them. Furthermore, even if an expensive chemical is used, the required amount of it is small and thus the chemical cost is low. Also, the chemical reactors can be operated in parallel and, therefore, mass production is possible for a product which is generated by reaction between liquids. For this reason, the invention can be widely applied to chemical plants, analyzers and so on.

According to the present invention, the time of reaction between liquids which do not mix with each other is substantially shortened. Hence, a smaller reaction container may be used and the minimum required volume of liquids for reaction is reduced. A smaller reaction container leads to overall equipment size reduction and a lower cost.

What is claimed is:

1. A chemical reactor comprising:
a sheath flow forming block including a plurality of nozzles arranged therein, said sheath flow forming block forming multiple sheath flows with two fluids that do not mix with each other;
a first inlet port through which a first fluid of said two fluids flows into said sheath flow forming block;
a plurality of second inlet ports, each of which is open to one of said nozzles inside said sheath flow forming block and through which a second fluid of said two fluids flows into said sheath flow forming block;
a contraction zone which simultaneously contracts said multiple sheath flows formed in said sheath flow forming block; and
a reaction flow channel which is connected with said contraction zone and is smaller in width than said sheath flow forming block;
wherein said sheath flow forming block is configured such that said two fluids led through said first inlet port and said second inlet ports into said sheath flow forming block are made into said sheath flows alternately arranged in a direction perpendicular to the flow direction.

2. The chemical reactor as claimed in claim 1, wherein a buffer tank with a flow channel sectional area larger than the flow channel sectional area of said sheath flow forming block is provided upstream of said sheath flow forming block.

3. The chemical reactor as claimed in claim 1, wherein a rectifying channel is provided upstream of said contraction zone in each of flow channels for said two fluids.

4. The chemical reactor as claimed in claim 1, wherein a plurality of said sheath flow forming blocks are arranged in parallel.

5. The chemical reactor as claimed in claim 4, wherein the lengths of the flow channels from said plural sheath flow forming blocks to an area of convergence at the downstream are equal.

6. The chemical reactor as claimed in claim 1, wherein said reaction flow channel located downstream of said sheath flow forming block has a profile formed with a straight line and a smooth curve.

7. The chemical reactor as claimed in claim 1, wherein, downstream of said reaction flow channel through which two kinds of fluids having an interface flow, a thin flow channel with a sectional area smaller than the sectional area of said reaction flow channel is provided and a thick flow channel with a sectional area larger than the sectional area of said reaction flow channel is provided downstream of said thin flow channel, and two outlet ports which differ in height vertically are provided downstream of said thick flow channel.

8. The chemical reactor as claimed in claim 7, wherein an area adjacent to at least one of said outlet ports is surface-treated.

9. The chemical reactor as claimed in claim 1, wherein, downstream of said reaction flow channel in which two kinds of liquids having an interface flow, one outlet port is provided for each liquid and a separation film having a plurality of holes with a sectional area of 0.01 mm² or less is provided between one outlet port and said reaction flow channel.

10. The chemical reactor as claimed in claim 1, wherein, downstream of said reaction flow channel in which two kinds of liquids having an interface flow, one outlet port is provided for each liquid, and a separation film having a plurality of holes with a sectional area of 1 mm² or less is provided between one outlet port and said reaction flow channel, and the inside of said holes and an area adjacent to said holes on a flow channel surface in which said holes are made are surface-treated.

11. The chemical reactor as claimed in claim 1, wherein, downstream of said reaction flow channel in which two kinds of liquids having an interface flow, one outlet port is provided for each liquid and one thin flow channel with a sectional area of 10 mm² or less is provided between one outlet port and said reaction flow channel.

12. The chemical reactor as claimed in claim 1, wherein, downstream of said reaction flow channel in which two kinds of liquids having an interface flow, one outlet port is provided for each liquid, and one hole with a sectional area of 100 mm² or less is provided between one outlet port and said reaction flow channel, and the inside of said holes and an area adjacent to said hole on a flow channel surface in which said holes are made are surface-treated.

13. The chemical reactor as claimed in claim 12, wherein an area adjacent to said hole on one outlet side is lipophilic-finished or water-repellent finished and an area adjacent to said hole on the other outlet side is hydrophilic-finished.

* * * * *